United States Patent [19]
Goble

[11] Patent Number: 6,039,734
[45] Date of Patent: Mar. 21, 2000

[54] ELECTROSURGICAL HAND-HELD BATTERY-OPERATED INSTRUMENT

[75] Inventor: Colin Charles Owen Goble, South Glamorgan, United Kingdom

[73] Assignee: Gyrus Medical Limited, Cardiff, United Kingdom

[21] Appl. No.: 09/065,091

[22] PCT Filed: Oct. 21, 1996

[86] PCT No.: PCT/GB96/02577

§ 371 Date: Jul. 27, 1998

§ 102(e) Date: Jul. 27, 1998

[87] PCT Pub. No.: WO97/15237

PCT Pub. Date: May 1, 1997

[30] Foreign Application Priority Data

Oct. 24, 1995 [GB] United Kingdom .................. 9521772

[51] Int. Cl.[7] .................................................. A61B 17/39
[52] U.S. Cl. ........................... 606/41; 606/42; 606/45; 606/49; 607/151
[58] Field of Search ............................. 606/35, 41, 42, 606/44, 45, 49; 607/145, 151

[56] References Cited

U.S. PATENT DOCUMENTS

| | | |
|---|---|---|
| 1,787,709 | 1/1931 | Wappler . |
| 1,814,791 | 7/1931 | Ende . |
| 2,894,512 | 7/1959 | Tapper . |
| 3,054,405 | 9/1962 | Tapper . |
| 3,197,612 | 7/1965 | Reich . |
| 3,234,356 | 2/1966 | Babb . |
| 3,478,744 | 11/1969 | Leiter . |
| 3,658,067 | 4/1972 | Bross . |
| 3,875,945 | 4/1975 | Friedman .................................. 606/45 |
| 4,271,837 | 6/1981 | Schuler . |
| 4,281,373 | 7/1981 | Mabille . |
| 4,463,759 | 8/1984 | Garito et al. . |
| 4,580,562 | 4/1986 | Goof et al. . |
| 4,657,016 | 4/1987 | Garito et al. . |
| 4,706,667 | 11/1987 | Roos . |
| 4,818,954 | 4/1989 | Flachenecker et al. . |
| 4,878,493 | 11/1989 | Pasternak et al. ........................ 606/45 |
| 4,909,255 | 3/1990 | Farin . |
| 5,007,908 | 4/1991 | Rydell . |
| 5,047,026 | 9/1991 | Rydell . |

(List continued on next page.)

FOREIGN PATENT DOCUMENTS

| | | |
|---|---|---|
| 0 530 400 | 3/1993 | European Pat. Off. . |
| 0 536 440 | 4/1993 | European Pat. Off. . |
| 558316 | 9/1993 | European Pat. Off. . |
| 42 17 999 | 12/1993 | Germany . |
| 42 22 769 | 1/1994 | Germany . |
| 42 37 321 | 5/1994 | Germany . |
| 88/01851 | 3/1988 | WIPO . |

OTHER PUBLICATIONS

Valleylab Publication: Advances in Bipolar Electrosurgery for Laparoscopic Surgery, pp. 1–4.
Mentor O & O, Inc. Publication: Introducing the Mentor Wet Field Cordless Coagulator, Instruction Manual, 7 pgs.
Odontosurge 2, 2 pg product description.
Patil et al., "Electroconvergent Cautery", Neurosurgery, vol. 35, No. 4, Oct. 1994, pp. 785–788.
Total Radiosurgery, Electrosurgery, and Bipolar with the Office Practice in Mind, 1 pg product description.
Servotome™ Classic System 50 Watts, Electrosurgery, Satelec, 2 pg product description.

*Primary Examiner*—Lee Cohen
*Attorney, Agent, or Firm*—Nixon & Vanderhye P.C.

[57] ABSTRACT

An electrosurgical instrument comprises a handpiece, a monopolar electrode unit having a single treatment electrode projecting from the handpiece, a radio-frequency generator and a battery within the handpiece for powering the generator. The generator has a single direct radio-frequency output patient connection through the treatment electrode. The return path between the generator and a patient is through an electrically conductive shield around the generator and forming part of the handpiece, the shield forming a capacitive coupling element between the generator and the surroundings. Preferably, the operating frequency of the generator is 5 MHz or greater.

23 Claims, 1 Drawing Sheet

U.S. PATENT DOCUMENTS

| | | |
|---|---|---|
| 5,047,027 | 9/1991 | Rydell . |
| 5,085,659 | 2/1992 | Rydell . |
| 5,133,721 | 7/1992 | Angulo . |
| 5,171,255 | 12/1992 | Rydell . |
| 5,196,007 | 3/1993 | Ellman et al. . |
| 5,217,458 | 6/1993 | Parins . |
| 5,254,117 | 10/1993 | Rigby et al. . |
| 5,306,238 | 4/1994 | Fleenor . |
| 5,330,469 | 7/1994 | Fleenor . |
| 5,342,356 | 8/1994 | Ellman et al. . |
| 5,395,368 | 3/1995 | Ellman et al. . |

…

ELECTROSURGICAL HAND-HELD BATTERY-OPERATED INSTRUMENT

This application is the National Stage of PCT Application Number PCT/GB96/02577, filed Oct. 12, 1996.

BACKGROUND OF THE INVENTION

This invention relates to an electrosurgical instrument having a monopolar electrode unit, and in particular to an instrument which is operable at high frequencies, typically in excess of 5 MHz.

A known electrosurgical system comprises a handpiece, a monopolar electrode unit having a single treatment electrode projecting from the handpiece, a generator unit, and a cable coupling the generator unit to the handpiece. Such systems are commonly used for various types of electrosurgery. Normally, a conductive pad is applied to the body of the patient and connected to a return terminal of the generator unit to provide a return path for electrosurgical currents. Disadvantages of this arrangement include the localisation of electrosurgical currents in tissue in the region of the return pad and, particularly at higher frequencies, the unpredictability of reactive components created by the cable between the generator and the handpiece, leading to unpredictable voltage levels at the electrode.

SUMMARY OF THE INVENTION

According to this invention, there is provided an electrosurgical instrument comprising a handpiece, a monopolar electrode unit having a single treatment electrode projecting from the handpiece, and a radio-frequency generator within the handpiece, wherein the generator has a single direct radio-frequency output patient connection for providing an active output connection between generator and patient and taking the form of a connection to the treatment electrode, and wherein the generator has no other direct radio-frequency output connection, the return path between generator and patient being provided for by indirect patient connection means including an electrically conductive shield around the generator and forming part of the handpiece, the shield forming a capacitive coupling element between the generator and the surroundings.

This allows the generator to be isolated from external elements other than the electrode. In particular, the generator has no other radio frequency output connection to, for example, an earthed element or to a return pad. By providing the generator within the handpiece, unpredictable impedance changes due to the effects of supplying radio-frequency currents through a cable are avoided. Radio-frequency return currents pass between the patient and the generator by stray capacitive coupling via a conductive shield located around the generator.

Preferably, the operating frequency of the generator is 5 MHz or greater. The higher the frequency, the greater the attainable current level due to the reduced reactance of the return path at raised frequencies. The generator may be powered from a battery within the handpiece. This minimises radiated interface.

The presence of an electrically conductive shield around the generator minimises the variation in stray capacitance caused by the user gripping the handpiece in different ways. The shield is preferably isolated from the generator and may form a tubular handpiece body, e.g. in the form of a metallic casing, or the handpiece body may be formed of an electrically insulative material which is metallised to provide the conductive shield. Where the metallisation layer is on the outside of the handpiece body, or the handpiece body is itself metallic, the outer metallic surface is preferably covered by an electrically insulating outer layer. Provision of the shield reduces stray capacitance variations because the capacitance between the relevant generator conductors and the shield is constant, and the shield provides a conductive body of constant area capacitively coupled to the patient.

The invention also includes a method of applying electrosurgical energy to a living body, the method comprising placing the electrode of an instrument as described above in contact with the body and activating the generator, the stray capacitance between the generator and the body providing a radio-frequency current return path.

BRIEF DESCRIPTION OF THE DRAWINGS

The invention will now be described by way of example with reference to the drawings in which.

DETAILED DESCRIPTION OF THE INVENTION

Figure 1:
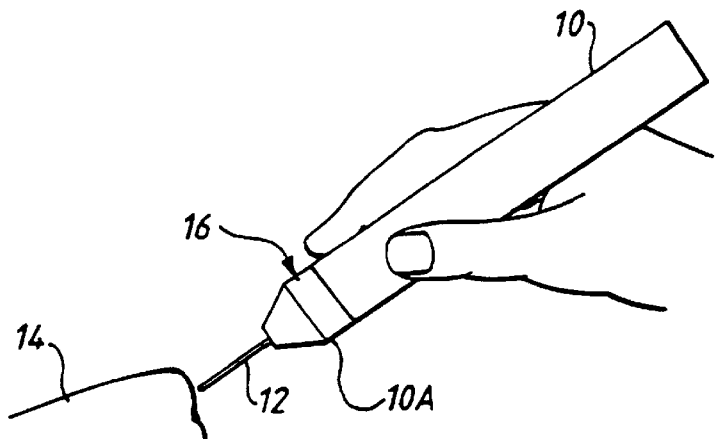
FIG. 1 is a diagram of an instrument in accordance with the invention, shown in use.

Referring to FIG. 1, an instrument in accordance with the invention comprises an elongate cylindrical handpiece 10 which may be held "pencil-fashion" as shown. One end portion 10A of the handpiece is tapered and an electrode unit in the form of a single treatment electrode 12 projects axially from that end so that it may be brought into contact with the body 14 of a patient. An activating switch 16 is provided on the tapered end portion 10A. The body 10 of the handpiece may be formed from sheet metal, and provided with an insulating covering made from, for instance, a film material. Alternatively, the handpiece body 10 may be moulded from an electrically insulative plastics material, and metallised either on the inner or the outer surface. If the metallisation is on the outer surface, an electrically insulating coating is provided to isolate the metallisation from the user's hand.

Figure 2:
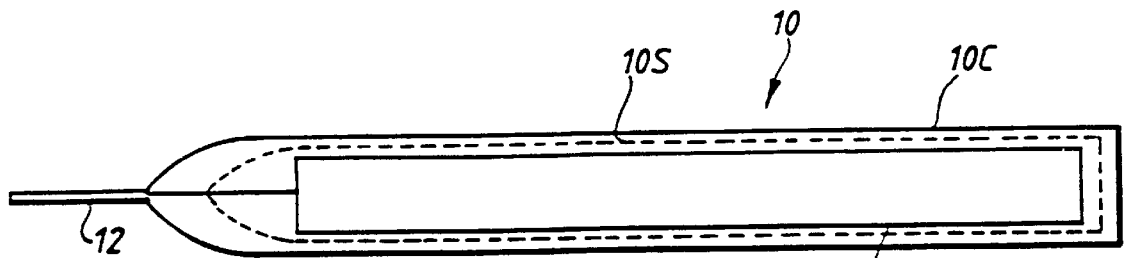
FIG. 2 is a diagrammatic longitudinal cross-section of the instrument.

In the diagrammatic cross-section of FIG. 2, the handpiece body 10 is shown as comprising the conductive shield 10S and an insulation case 10C. An internal electronic unit 18 comprising a radio frequency generator and a battery is contained within the shield 10S. Although it is not essential for the electronic unit 18 to be completely encased by the shield 10S as shown, it is preferable that at least the generator part lies with the lengthwise extent of the shield. The shield 10S has a number of useful properties. The internal electronic unit 18 has a non-uniform mass and distribution within the case, with different potentials relative to earth. The shield 10S provides a uniform surface of the same or uniform potential. By making the insulation layer 10C a minimum size and thickness, the size of the shield can be made a maximum and capacitive coupling both to the patient, the user and external earthed objects can be made a maximum.

By making the shield circumferentially continuous, the internal electronics are also effectively screened against the potentially interfering levels of RF radiation. Making the case out of metal to provide the shield function also has an added advantage in that the shield provides uniform heat distribution and therefore improves the dissipation of power generated within the electronic unit due to inefficiencies.

Figure 3:
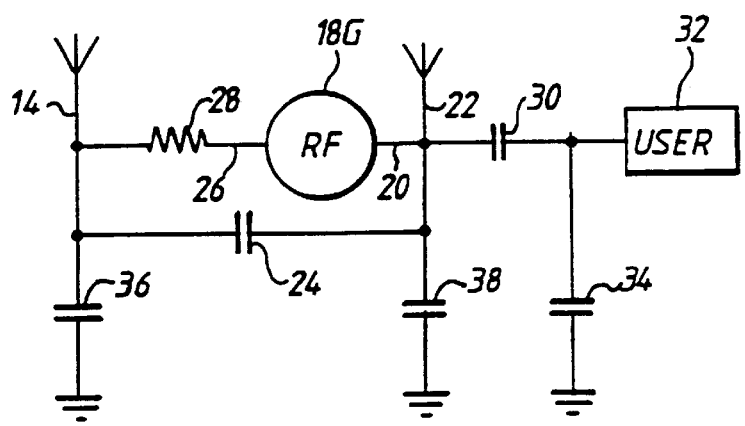
FIG. 3 is an equivalent electrical circuit diagram of the instrument when in use.

Referring to FIG. 3, the equivalent circuit of the instrument when in use is now considered. Inside the handpiece body, there is provided a radio frequency (RF) generator 18G operable at a frequency of 5 MHz or higher (switch 16 and shield 10S are not shown in FIG. 3). The generator has an output connection coupled to the electrode 12 (FIG. 1), and has no other output connection. Conductive elements of the generator 18G (the elements are shown figuratively by the reference 20 in FIG. 3) act as an antenna 22 and are capacitively coupled, indirectly via the conductive shield 10S of the handpiece body 10 (see FIGS. 1 and 2) via capacitance 24 to the patient 14, represented as a second antenna in FIG. 3. The electrode to tissue interface is represented by line 26. Thus, when in use, the active output connection of the generator 18 is connected to the patient 14 through the tissue being operated on, the resistance of this tissue being represented by resistance 28 in FIG. 3. The value of this resistance is typically 1 kΩ, and can drop to as low as 100 Ω.

The radiating conductors 20 of the generator 18G are also capacitively connected to the user by capacitance 30, which is the series combination of the generator-to-shield and shield-to-user capacitances, the user 32 being, in turn capacitively coupled to ground as represented by capacitor 34. Since the patient 14 is also capacitively coupled to ground (as represented by capacitor 36 in FIG. 3), there exists an indirect as well as a direct capacitive path between the user 32 and the patient 14. Similarly, there is an indirect path from generator conductive elements 20 through the capacitance 38 of the handpiece body 10 (specifically the shield 10S) to ground and the series capacitance 36 between the patient 14 and ground. The total capacitance between the generator 18G and the patient 14 resulting from the direct generator-to-patient capacitance 24, handpiece-body-to-user capacitance 30, user-to-ground, handpiece body-to-ground, and patient-to-ground capacitances 34, 38 and 36 respectively, is at least 15 pF.

Not shown in the drawings is a battery which is also housed within the handpiece body 10. This is preferably a nickel-cadmium or lithium-ion battery, rechargeable via terminals in the opposite end of the body 10 from the electrode 12.

This instrument is primarily, but not exclusively, intended for fine surgical work, such as spinal, neurological, plastic, ear-nose-and-throat and dental surgery, and office procedures.

What is claimed is:

1. An electrosurgical instrument comprising a handpiece, a monopolar electrode unit having a single treatment electrode projecting from the handpiece, and a radio-frequency generator within the handpiece, the handpiece including an electrically conductive shield around the generator as a capacitive coupling element between the generator and the surroundings, and wherein the generator has no radio-frequency connections other than a single radio-frequency output connection to the treatment electrode for providing an active output connection between the generator and a patient and, in use, a return path between the generator and the patient provided by said capacitive coupling.

2. An instrument according to claim 1, wherein the operating frequency of the generator is 5 MHz or greater.

3. An instrument according to claim 1, wherein the handpiece has a battery for powering the generator.

4. An instrument according to claim 1, wherein the shield is isolated from the generator.

5. An instrument according to claim 1, wherein the shield forms a handpiece body.

6. An instrument according to claim 5, wherein the handpiece body is a metallic tube with an insulative film applied to its outer surface.

7. An instrument according to claim 1, wherein the shield is generally tubular and the generator is contained within the shield length.

8. An instrument according to claim 1, wherein the handpiece has a handpiece body formed of electrically insulative material and the shield is a metallization layer on the handpiece body.

9. An instrument according to claim 8, wherein the metallization layer is on the outside of the handpiece body and is covered by an electrically insulative outer layer.

10. A method of applying electrosurgical energy to a living body comprising placing the electrode of an instrument according to claim 1 in contact with the body, and activating the generator, the stray capacitance between the generator and the body providing a radio-frequency current return path.

11. An electrosurgical instrument comprising a housing, an active tissue treatment electrode supported relative to the housing and extending externally thereof, thereby to enable manipulation of the active electrode by gripping the housing, an electrosurgical generator located within the housing and having first and second output terminals, the first output terminal being connected to the active electrode, and means providing a capacitive coupling path for capacitively coupling the second output terminal to the active electrode when the active electrode is in physical contact with tissue, the capactive coupling providing sufficient flow of alternating current to enable tissue modification by the active electrode, and the coupling path excluding earth or any trailing leads from the instrument.

12. An electrosurgical instrument according to claim 11, further comprising a conductive shield within which the generator is located, the shield enhancing the capacitive coupling of the active electrode and the second generator output terminal.

13. An electrosurgical instrument according to claim 12 wherein the conductive shield is provided by the housing.

14. An electrosurgical instrument according to claim 11 wherein the radio freguency generator operates at a frequency of greater than 5 MHz.

15. An electrosurgical instrument according to claim 11 further comprising a battery located within the housing, the battery powering the generator.

16. An electrosurgical instrument according to claim 15 further comprising a conductive shield within which the generator is located, the shield enhancing the capacitive coupling of the active electrode and the second generator output terminal.

17. An electrosurgical instrument according to claim 16 wherein the shield is provided by the housing.

18. An electrosurgical instrument comprising a housing, an electrosurgical generator located within the housing, the generator having first and second output terminals, an active tissue treatment electrode supported relative to the housing to enable the active electrode to be manipulated by gripping the housing, the active electrode being connected to the first output terminal of the generator, and a capacitive coupling between the second output terminal and the active electrode enabling a sufficient flow of alternating current along a path which includes only: a) the active electrode, b) tissue in the region of the active electrode and c) elements connected to the second output terminal which are integral with the instrument, to enable tissue modification by the active electrode.

19. An electrosurgical instrument according to claim 18, wherein the generator operates at a frequency of greater than 5 MHz.

20. An electrosurgical instrument according to claim 18 further comprising a battery within the housing to power the generator.

21. A method of treating a patient using an electrosurgical instrument having an electrosurgical generator which produces a radio frequency output across a pair of output terminals, and an active tissue treatment electrode connected to a first output terminal of the pair of terminals, the method comprising the steps of:

bringing tissue of the patient into contact with the first output terminal of the generator by bringing the active electrode into physical contact with the tissue; and capacitively coupling the active electrode and a second output terminal of the pair of terminals via tissue in the region of the active electrode, and providing, by virtue of such capacitive coupling, a path for the flow of sufficient alternating current between the active electrode and the second output terminal to enable tissue modification by the active electrode, the path excluding earth and any trialing leads from the instrument.

22. A method according to claim 21 wherein the generator is located within a housing to which the active electrode is secured, thereby enabling the housing to be gripped for the purpose of manipulating the active electrode, the method further comprising the steps of: supplying power to the generator from a battery located within the housing, and gripping the housing in order to manipulate the active electrode in the region of the treatment site.

23. A method according to claim 22 wherein the second generator output terminal is connected to a conductive shield, and the path along which capacitive coupling between the active electrode and the second generator output terminal occurs includes the conductive shield.

* * * * *